United States Patent [19]

Morgan

[11] Patent Number: 6,094,596
[45] Date of Patent: Jul. 25, 2000

[54] TRANSVENOUS DEFIBRILLATION LEAD SYSTEM FOR USE IN MIDDLE CARDIAC VEIN

[75] Inventor: John Morgan, Stockbridge, United Kingdom

[73] Assignee: Angeròn Corporation, Minneapolis, Minn.

[21] Appl. No.: 09/100,904

[22] Filed: Jun. 19, 1998

[51] Int. Cl.$^7$ ................................................... A61N 1/39
[52] U.S. Cl. ................................................ 607/5; 607/122
[58] Field of Search ................................... 607/4, 5, 122, 607/123

[56] References Cited

U.S. PATENT DOCUMENTS

| | | |
|---|---|---|
| 4,928,688 | 5/1990 | Mower . |
| 4,932,407 | 6/1990 | Williams ................................ 128/419 |
| 5,282,845 | 2/1994 | Bush et al. . |
| 5,304,218 | 4/1994 | Alferness . |
| 5,314,430 | 5/1994 | Bardy . |
| 5,431,683 | 7/1995 | Bowald et al. ............................ 607/5 |
| 5,433,729 | 7/1995 | Adams et al. . |
| 5,531,779 | 7/1996 | Dahl et al. . |
| 5,545,204 | 8/1996 | Cammilli et al. . |
| 5,551,426 | 9/1996 | Hummel et al. . |
| 5,643,338 | 7/1997 | Bornzin et al. ......................... 607/123 |
| 5,755,765 | 5/1998 | Hyde et al. . |
| 5,755,766 | 5/1998 | Chastain et al. . |

FOREIGN PATENT DOCUMENTS

| | | |
|---|---|---|
| 93 118002 | 5/1993 | France . |
| 93 118004 | 5/1993 | France . |
| PCT/US97/17198 | 9/1997 | WIPO . |
| PCT/US97/17233 | 9/1997 | WIPO . |
| PCT/US09/01312 | 1/1998 | WIPO . |
| PCT/US98/01362 | 1/1998 | WIPO . |
| PCT/US98/01363 | 1/1998 | WIPO . |

OTHER PUBLICATIONS

Lau et al. Initial Clinical Experience with an Implantable Human Atrial defibrillator. PACE 20:220–225, 1997.

Heisel et al. Low–Energy Transvenous Cardioversion of Atrial Fibrillation using a single atrial lead system. J of Cardiovascular Electrophysiology 8:6:607–614, 1997.

Lok et al. Clinical Shock Tolerability and effect of different right atrial electrode locations on efficacy of low energy human transvenous atrial defibrillation using an implantable lead system. JACC 30:5:1324–1330, 1997.

Bardy et al. A prospective randomized comparison in humans of the unipolar pectoral defibrillation system with one incorporating an additional electrode in the coronary sinus. Circ 88:4:2: I–216, 1993.

*Primary Examiner*—Kennedy Schaetzle
*Attorney, Agent, or Firm*—Brad D. Pedersen

[57] ABSTRACT

A highly efficacious defibrillation lead system and method of use in the middle cardiac vein. The lead system includes a catheter shaft having a plurality of electrode channels and a venous electrode within each channel. A lead wire is electrically interconnected to each venous electrode and extends through the associated electrode channel to the distal end of the shaft. The lead system can be efficiently implanted in the middle cardiac vein when the electrodes are in retracted positions within the channels. After the lead system is implanted, the electrodes are moved to branched deployed positions beyond a distal end of the shaft and into a plurality of tributaries of the middle cardiac vein. The branched electrode distribution in the middle cardiac vein is achieved with relatively little trauma during deployment and enables successful defibrillation with reduced defibrillation threshold energy to enhance the overall defibrillation procedure.

8 Claims, 3 Drawing Sheets

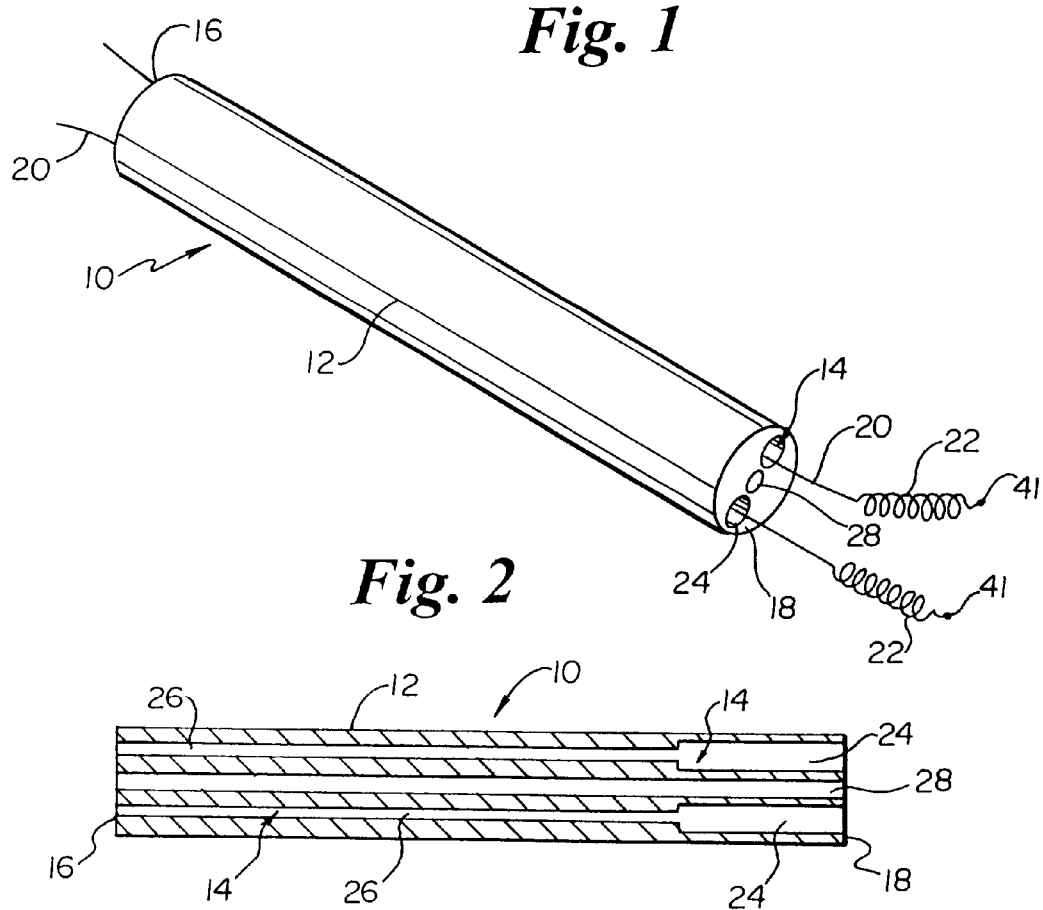
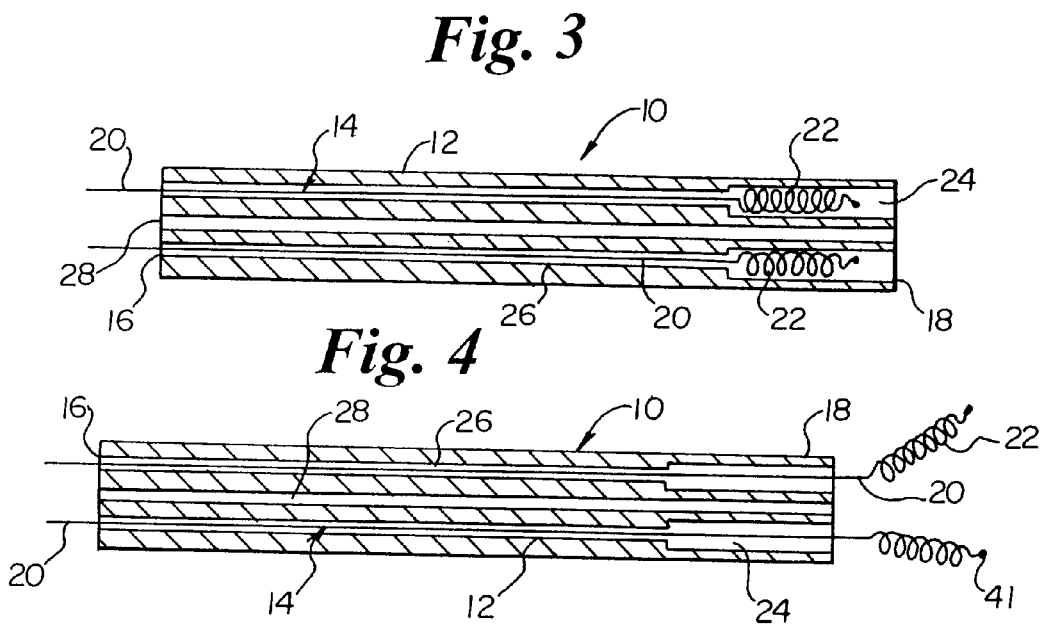

TRANSVENOUS DEFIBRILLATION LEAD SYSTEM FOR USE IN MIDDLE CARDIAC VEIN

FIELD OF THE INVENTION

The present invention relates to transvenous leads primarily for use in connection with an implantable cardioverter defibrillator. More particularly, the present invention relates to a transvenous defibrillation lead system for use in the cardiac vein branches of the heart, especially the middle cardiac vein and associated posterior cardiac veins, as well as implantable defibrillator devices and methods which have the ability to utilize such a lead system.

BACKGROUND OF THE INVENTION

Implantable defibrillators are well known. A critical element of these devices is the lead system which provides electrodes to sense the electrical activity of the heart and to deliver an appropriate electrical stimulation in the event the device detects an abnormal rhythm. The most popular type of lead system for use with these devices is a transvenous lead system in which the electrodes are carried on the distal end of an elongated catheter that is inserted into a vein near the heart and then moved into position, typically in either the right atrium or right ventricle, after which the proximal end is connected to the device in order to provide an electrical connection between the electrodes and the device.

In a typical configuration for an implantable defibrillator, for example, the transvenous lead may have a pacing tip electrode at the very most distal end which is positioned in the apex of the right ventricle. A defibrillation coil electrode spaced back from the pacing tip is positioned to lie along the bottom and side of the right ventricle. Sensing and pacing can be accomplished in a unipolar manner between the tip electrode and the defibrillation electrode. Alternatively, sensing and pacing can be accomplished in a bipolar manner by providing an additional ring electrode spaced adjacent from the tip electrode. Defibrillation can be accomplished between the defibrillation electrode in the right ventricle and the housing of the device located in the pectoral region or a subcutaneous electrode located on the left side of the body. For dual chamber applications in which pacing and sensing is needed in both the right atrium and the right ventricle, an additional catheter carrying a pair of pace/sense electrodes is typically located in the right atrium.

Although the typical transvenous lead system offers many advantages in terms of ease of implantation and good sensing, it is well known that a transvenous defibrillation lead system is less efficient than a lead system using epicardial patches. However, epicardial patch electrodes have the disadvantage of requiring open heart surgery for implantation. Because the effectiveness of both the electrical sensing and stimulation of these devices depends upon the characteristics and performance of the lead system, many alternative lead systems for implantable defibrillators have been proposed.

In U.S. Pat. Nos. 4,932,407 and 5,014,696, a lead system is described in which a transvenous lead is positioned in the coronary sinus vein, a vein which is accessed through the right atrium. To accomplish defibrillation, these patents teach the delivery of a defibrillation countershock between defibrillation electrodes positioned in the right ventricle and the coronary sinus plus a subcutaneous electrode. In U.S. Pat. No. 5,099,838, a similar lead system is described in which delivery of a defibrillation countershock is taught between a coronary sinus electrode and a subcutaneous electrode. Subsequent research by the inventor of the '838 patent suggested that the addition of a coronary sinus electrode did not increase the overall effectiveness of defibrillation as compared to a conventional lead system. Bardy, "A Prospective Randomized Comparison in Humans of the Unipolar Pectoral Defibrillation System with one Incorporating an Additional Electrode in the Coronary Sinus," *Circulation* Vol. 88, No. 4, Part 2, Oct. 1993, 1155.

In U.S. Pat. Nos. 5,314,430, 5,348,021, 5,350,404, 5,433, 729 and 5,476,498, lead systems for an atrial defibrillator are described in which electrodes placed in the coronary sinus and its extension, which wraps around to the front of the heart and is known as the great vein, are used in conjunction with electrodes in the right ventricle or super vena cava, as well as subcutaneous electrodes, to defibrillate the atria. Because these lead systems are used primarily for defibrillating the atria or upper chambers of the heart, the coronary sinus vein and the great vein which wrap around the atria provide an ideal location for an atrial defibrillation lead system. Unfortunately, initial clinical experiences with these types of atrial defibrillation lead systems have shown that, while these lead systems are effective for atrial defibrillation, the pain threshold associated with the atrial defibrillation using these lead systems is often not tolerable. Lau et al., "Initial Clinical Experience with an Implantable Human Atrial Defibrillator," *PACE*, Vol. 20, Jan. 1997, Part II, pp 220–25; Heisel et al., "Low-Energy Transvenous Cardioversion of Atrial Fibrillation Using a Single Atrial Lead System," *Journal of Cardiovascular Electrophysiology*, Vol. 8, No. 6, June 1997, pp. 607–14; and Lok et al., "Electrode Sites for Transvenous Atrial Fibrillation," *JACC*, Vol. 30, No. 5, Nov. 1997, 1324–30.

In U.S. Pat. Nos. 5,755,765 and 5,755,766, a transvenous cardiac lead is described for use in the coronary sinus and great vein. This lead is provided with an internal lumen that is open at the distal end to allow a secondary electrode to be inserted through the lumen and extended beyond the distal end of the lead. The lead is also shown as having a reduced diameter at its most distal section. Disclosed techniques for implanting the lead in the coronary sinus include temporarily fixing the lead within a guiding catheter or using a guide wire in the open lumen. While this lead system is primarily intended for use in as part of a technique to pace both the right and left ventricles in an effort to improve the hemodynamic efficiency of the heart, it is also disclosed that the electrodes on this lead system may be used for defibrillation. Other pacing leads which are adapted for implantation in the coronary sinus and great vein are described in U.S. Pat. Nos. 5,545,204 and 5,755,761. As with the lead systems for atrial defibrillators, the objective of these pacing leads is to wrap around to the anterior or front side of the heart with the distal end of the lead.

In PCT Appl. No. WO 98/13102 a pacing lead is disclosed as part of a combination pacing/defibrillation system in which the pacing lead is introduced into the coronary sinus, then into the great cardiac vein, and then into the ascending limb of either the anterior cardiac vein or the posterior cardiac vein. The objective of the placement of this pacing lead is to locate the electrode as close as possible to the apex of the left ventricle. In PCT Appl. No. WO 98/14241 a pacing lead is disclosed for providing multisite anodal stimulation to improve cardiac output. One embodiment of the lead is lodged deep in the great rein and coronary sinus and optionally extending toward the ventricular apex into the great or middle cardiac vein.

Most transvenous defibrillation lead systems are constructed of a catheter tube having one or more lumens through which conductor wires are strung and then attached to ring or coil electrodes located near the distal end of the tube. Several alternative constructions for transvenous lead systems also have been proposed. In U.S. Pat. No. 5,304, 218, a transvenous lead system is described in which the catheter lead is placed in position using an over-the-wire guide. In U.S. Pat. Nos. 5,282,845 and 5,551,426, multiple precurved electrode segments are deployed from the distal end of the catheter tube within a chamber of the heart in an effort to create a single common electrode having a larger effective surface area. Similarly, in U.S. Pat. Nos. 5,203,348 and 5,360,442, a single subcutaneous electrode is provided with multiple finger elements that are electrically connected in common to emulate a single electrode having a larger effective surface area. In U.S. Pat. No. 5,531,779, a stent type of defibrillation electrode is disclosed which expands to conform to the interior of a vein.

While numerous transvenous defibrillation lead systems have been proposed, there are certain patients for which the defibrillation lead system is not as efficient as would be desired. As a result, the defibrillation threshold for successfully defibrillating these patients is larger than may be acceptable in terms of an appropriate safety margin for a given implantable defibrillator. It would be advantageous to provide a transvenous defibrillation lead system which had improved characteristics and performance over existing transvenous defibrillation systems, particularly for patient who exhibit high defibrillation thresholds with existing transvenous defibrillation lead systems.

SUMMARY OF THE INVENTION

The present invention is a highly efficacious middle cardiac vein defibrillation method and lead system for human patients. One embodiment of the method includes implanting a plurality of electrodes in the patient, including an electrode in the middle cardiac vein of the patient's heart. A cardioverter defibrillator for treating cardiac dysrhythmias is also implanted in the patient, and electrically interconnected to the electrodes. When a dysrhythmia is sensed, the defibrillator delivers electrical defibrillation countershocks to the patient's heart through the implanted electrodes, including the electrode in the middle cardiac vein.

Defibrillation through the use of an electrode implanted in the middle cardiac vein and its tributaries offers a number of important advantages. Blood pressures in the middle cardiac vein are relatively low, so the presence of the lead system is tolerated by this cardiac vasculature. Defibrillation shocks using electrodes implanted in the middle cardiac vein will effectively provide a current path from the posterior side through the middle of the heart. Successful defibrillation can thereby be achieved with reduced defibrillation threshold energy (DFT) to enhance the efficacy of the overall defibrillation procedure.

Another embodiment of the invention is a lead system adapted for branched deployment in a cardiac venous system such as the middle cardiac vein and its tributaries. The lead system includes a catheter shaft with a plurality of electrode channels, a venous electrode within each channel, and lead wires electrically interconnected to each electrode and extending through the associated channel to the distal end of the shaft. The electrodes are movable between a retracted position within the channel and a branched deployed position. In the deployed position the electrodes are outside the channel and beyond the distal end of the shaft into a plurality of the venous branches.

The lead system, especially when used in the middle cardiac vein and its tributaries, provides a number of important advantages. It can, for example, be relatively easily delivered to a defibrillation site. The electrodes can also be relatively easily deployed from the catheter shaft. The branched electrode distribution enhances the efficacy of defibrillation procedures by effectively simulating an epicardial patch electrode. Furthermore, this branched electrode distribution can be achieved with relatively little trauma to the vasculature during deployment.

BRIEF DESCRIPTION OF THE DRAWINGS

FIG. 1 is an isometric view of an implantable lead system in accordance with the present invention.

FIG. 2 is a cross sectional view of the catheter shaft of the lead system shown in FIG. 1.

FIG. 3 is a cross sectional view of the lead system shown in FIG. 1 with the electrodes in the retracted position.

FIG. 4 is a cross sectional view of the lead system shown in FIG. 1 with the electrodes in the deployed position.

DETAILED DESCRIPTION OF THE PREFERRED EMBODIMENTS

Figure 9:
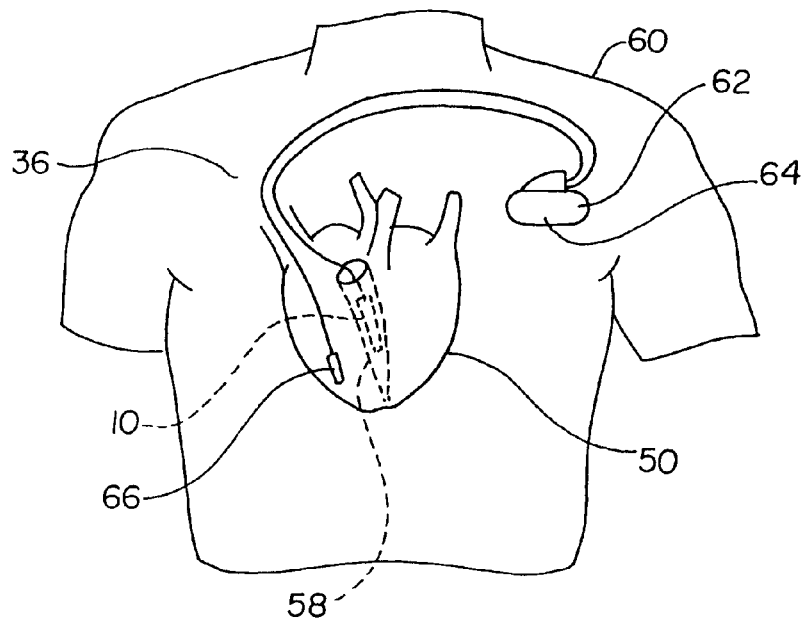
FIG. 9 is a diagrammatic illustration of a human torso and heart, having the lead system shown in FIG. 1 and a defibrillator implanted therein and electrically interconnected.

An implantable defibrillation lead system 10 in accordance with the present invention is illustrated generally in FIGS. 1–4. As shown, lead system 10 includes an elongated and generally cylindrical catheter body or shaft 12 having a plurality of electrode channels such as lumens 14 (two are shown) extending between its proximal end 16 and distal end 18. An electrical lead wire 20 having an electrode 22 on its distal end is slidably positioned within each electrode lumen 14. In the illustrated embodiment, the electrodes 22 are coil-type members having a diameter which is greater than the diameter of the lead wires 20. The electrode lumens 14 have an electrode-receiving portion 24 on the distal end 18 of the catheter shaft 12 and a lead-receiving portion 26 which extends between the electrode-receiving portion and the proximal end 16 of the catheter shaft. The electrode-receiving portions 22 of the lumens 14 have a diameter which is greater than the diameter of the lead-receiving portion 24, and are sized to receive and enclose the electrodes 22 within the distal end 18 of the catheter shaft 12 when the electrodes are in the retracted positions shown in FIG. 3. After the lead system 10 is transluminally delivered to a desired location within the patient (e.g., in the manner described below), the electrodes 22 can be slidably moved to their deployed positions out of the lumens 14 and beyond the distal end 18 of the catheter shaft 12. FIGS. 1 and 2 illustrate the electrodes 22 in their deployed positions. The illustrated embodiment of catheter shaft 12 also includes a stylet lumen 28 which extends through the center of the shaft between the proximal end 16 and distal end 18. A stylet or guidewire (not shown in FIGS. 1–4) extending through the lumen 28 can be used to guide the catheter shaft 12 during transvenous delivery of the lead system 10. At proximal end 16, conventional connectors (not shown) can be used to electrically and mechanically connect lead system 10 to a defibrillator or other similar implantable medical device (e.g., as shown in FIG. 9).

Catheter shaft 12 can be formed from polymers such as silicone, polyurethane or other suitable implantable biocompatible materials. The catheter shaft 12 is sized to allow it to be transvenously delivered to a desired treatment site through the desired vessel. Lead wires 20 can be formed from materials and have other characteristics (e.g., dimensions and flexibility) currently known or used, or subsequently developed, for defibrillator lead wires. A tear drop-shaped or other blunt tip 41 can be formed on the distal end of the electrodes 22 to minimize trauma to vessels during deployment of the electrodes. The tips 41 can, for example, be formed from biocompatible polymers or metal alloys.

Figure 5:
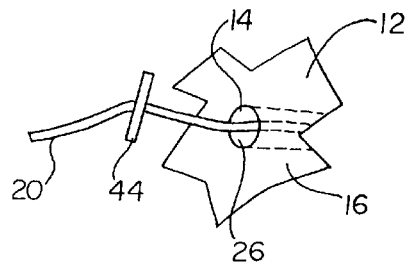
FIG. 5 is a detailed view of the proximal end of the lead system shown in FIG. 1, illustrating a collar on the lead wire.

Although conventional coil-type defibrillation electrodes 22 are shown in FIGS. 1, 3, 4 and 8, other currently known or used, or subsequently developed, electrodes suitable for implantable defibrillators can be incorporated into lead system 10. Lead wires 20 and/or electrodes 22 can also be formed (e.g., pre-bent or formed from shape-memory materials) and oriented within the lumens 14 in such a manner that when the electrodes are deployed from the catheter shafts 14 they will extend outwardly from the longitudinal axis in the lumens in predetermined directions and distances within the venous system of the patient. As described in greater detail below, this branched deployment enables the controlled spatial distribution of the electrodes within the venous system, thereby allowing the electrodes to be positioned at a number of desired locations in different vein branches. Alternatively (or in combination with the formed lead wires), the lumens 14 can be nonlinear or oriented non-parallel to the central longitudinal axis of the catheter shaft 12 to cause the desired branched deployment of the electrodes. As shown in FIG. 5, a structure such as collar 44 having dimensions greater than those of lumens 14 can be located on the ends of the lead wires 20 extending from the proximal end 16 of the catheter shaft 12. The collars 44 are securely mounted to the lead wires 20 at locations which cause the collars to engage the proximal end 16 of the catheter shaft and limit further motion of the lead wire when the electrode 22 is advanced to the desired deployed state. In other embodiments (not shown) structures within lumens 14 cooperate with the lead wires 20 to control the distance to which the lead wires can be deployed. Although two lead wires 20 and electrodes 22 (and associated lumens 14 in the catheter shaft 12) are shown in the illustrated embodiments, a greater number can be used as appropriate for the application.

Figure 6:
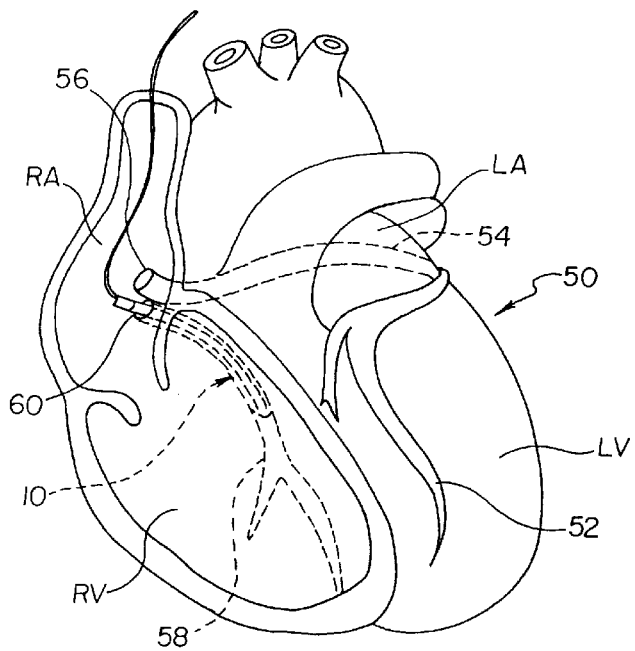
FIG. 6 is a diagrammatic view of the back side of a human heart, with portions shown in section, illustrating the lead system shown in FIG. 1 implanted in the middle cardiac vein.
Figure 7:
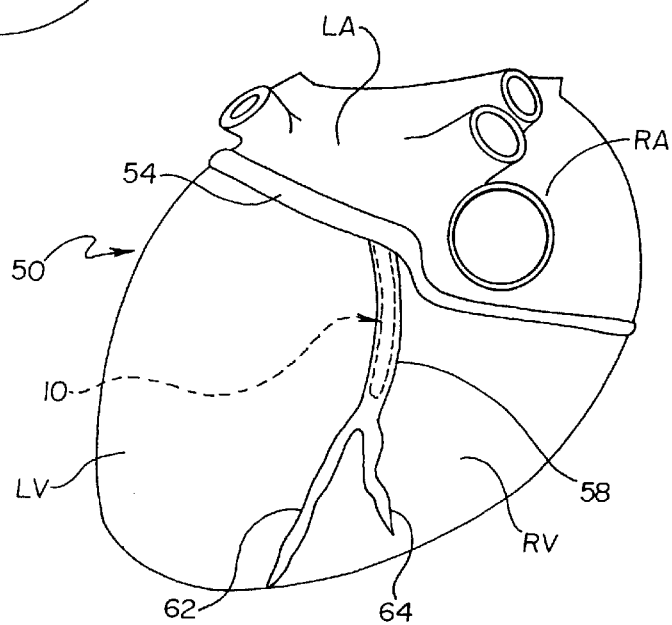
FIG. 7 is a diagrammatic view of the front side of a human heart, illustrating the lead system shown in FIG. 1 implanted in the middle cardiac vein.

The front and back sides of a human heart 50 having the lead system 10 implanted therein are illustrated in FIGS. 6 and 7, respectively. It will be understood that the following description of the cardiac venous system is based upon the observations and knowledge of the inventor and that the venous anatomy of the human heart is presently not well understood in the literature. Most anatomy textbooks utilize a stylized and simplified representation of only the primary branches of the cardiac venous system due to significant anatomical differences among individual, particularly in the secondary cardiac veins. Although there are differences in the cardiac arterial structure in terms of dimension or exact location of cardiac artery branches, there is far less variability in the actual branching relationship of primary and secondary arteries, as compared to the cardiac venous system. Accordingly, the exact nature and classification of the primary and secondary cardiac veins will be the subject of additional research.

The four primary chambers of heart 50 are the right atrium RA, right ventricle RV, left atrium LA and left ventricle LV. A relatively large descending branch 52 of the great cardiac vein 54 extends upwardly on the anterior side of the heart 50 at a location generally between the right ventricle RV and left ventricle LV. At a location generally between the left atrium LA and left ventricle LV the branch 52 wraps around the left side of the heart and extends across the posterior of the heart where it joins the great vein 54. Great vein 54 extends across the back side of heart 50 at a location generally between the left atrium LA and left ventricle LV to the coronary sinus 56 where it opens into the right atrium at CS ostium 57.

The middle cardiac vein 58 and its tributaries extend upwardly along the inferior interventricular groove, straddling the inferior aspect of the interventricular septum (i.e., at a location generally between the left ventricle LV and right ventricle RV on the back side of the heart 50). It has been observed that many texts describe the middle cardiac vein 58 as draining into the coronary sinus 56. This description is likely based at least in part on the fact that in postmortem specimens with venous collapse it is difficult to see the ostium of the middle cardiac vein on the endocardial aspect. However, as perhaps best shown in FIG. 6, the middle cardiac vein 58 opens directly into the right atrium RA at an MCV ostium 60 generally inferior to the coronary sinus ostium 57 and as much as 1 cm from the coronary sinus. MCV ostium 60, although relatively small compared to the ostium 57 of the coronary sinus 56 and difficult to see after venous collapse following death, is reasonably large. The middle cardiac vein 58 has a number of branches or tributaries, including the relatively large tributaries 62 and 64 which extend generally upwardly into the middle cardiac vein from locations adjacent to the bases of the left ventricle LV and right ventricle RV, respectively. As previously indicated, it will be understood that the relationship of the coronary sinus ostium 57 and the middle cardiac vein ostium 60 is variable and patient dependent. Existing literature is unclear as to the definition, for example, of where the right atrium becomes the coronary sinus ostium 57.

The inventor has discovered that it is possible to position a lead system 10 within the middle cardiac vein 58 via MCV ostium 60 without utilizing the CS ostium 57 of the coronary sinus 56. Whereas existing transvenous defibrillation electrodes have been introduced into cardiac veins via the coronary sinus 56, the present invention is able to reliably deploy a defibrillation electrode in the middle cardiac vein 58 regardless of the precise venous anatomy of a given patient and without the necessity of utilizing the CS ostium 57 of the coronary sinus 56. In practical terms as confirmed angiographically, the coronary sinus 56 remains uncompromised by cannalization of the MCV ostium 60 and available for ingress of electrode or other appartus to be placed in the coronary sinus 56.

Figure 8:
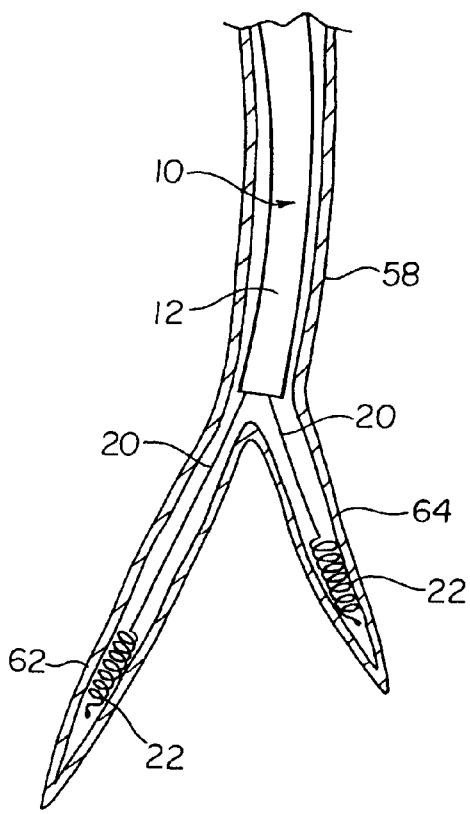
FIG. 8 is a detailed sectional view of the middle cardiac vein of a human heart, having the lead system shown in FIG. 1 implanted therein with the electrodes deployed.

As shown in FIG. 6, the lead system 10 is transvenously delivered to the right atrium RA of a patient with the electrodes 22 in the retracted position. From the right atrium RA the catheter shaft 12 is inserted, distal end 18 first, into the ostium 60 of the middle cardiac vein. The lead system 10 is then transvenously moved into the desired position and orientation in the middle cardiac vein 58. Although not shown in FIGS. 6 and 7, a stylet or guide wire which extends through the stylet lumen 28 can be used in a conventional manner during the delivery of the lead system 10. After the catheter shaft 12 is positioned and oriented in a desired manner, the ends of the lead wires 20 extending from the proximal end 16 of the catheter shaft can be advanced into the catheter shaft to deploy the electrodes 22. As shown in FIG. 8, the electrodes can be advanced into different branches (e.g., branches 62 and 64) of the middle cardiac vein 58. If the catheter shaft 12 is oriented in a predetermined manner and the lead system is configured in a manner described above to control the spatial distribution of the deployed electrodes 22, the electrodes will advance into the desired branches upon deployment.

FIG. 9 is a diagrammatic illustration of a human torso 60 and heart 50 after the lead system 10 is implanted in the middle cardiac vein 58. An implantable cardioverter defibrillator (ICD) 62 having an outer housing which functions as a CAN electrode 64 also is shown, implanted in the pectoral region of the chest of the patient. ICD 62 can be a conventional or otherwise subsequently known or developed device such as that disclosed in the Kroll et al. U.S. Pat. No. 5,405,363 which is hereby incorporated by reference in its entirety. ICD 62 is electrically interconnected to lead system 10 and to a conventional right ventricular apex (RVA) electrode 66. Tests have demonstrated that defibrillation using the middle cardiac vein (MCV), RVA and CAN electrode configuration shown in FIG. 9 can be efficaciously performed at lower defibrillation threshold energy than conventional RVA and CAN electrode configurations. In one embodiment, lead wires 20 of lead system 10 are electrically interconnected, enabling ICD 62 to simultaneously energize all electrodes 22. In other embodiments, the lead wires 20 are independently electrically interconnected to ICD 62. Defibrillation shocks delivered by some or all of electrodes 22 can thereby be sequenced and staggered in time.

In other embodiments (not shown), defibrillation can be performed using an electrode such as those of lead system 10 in the middle cardiac vein (MCV) in combination with other electrode configurations currently known or used or subsequently developed. It is, for example, anticipated that defibrillation can be efficaciously performed using MCV and CAN electrodes without the RVA electrode. Other defibrillation electrode combinations include MCV RVA and subcutaneous (SUBQ) electrodes, MCV, RVA, CAN and SUBQ electrodes, and MCV and superior vena cava (SVC) electrodes. These and other electrode configurations, as well as a range of patterns of pulses which can be applied to the electrodes, are disclosed in the Anderson et al. U.S. Pat. No. 5,376,103 which is hereby incorporated by reference in its entirety.

Lead system 10 offers a number of important advantages. The lead system can, for example, be relatively easily delivered to a desired defibrillation site. The catheter shaft is an efficient mechanism for simultaneously delivering a plurality of electrodes. The electrodes can also be relatively easily deployed from the catheter shaft. In addition, the branched distribution of the electrodes enhances the efficacy of defibrillation procedures performed by the lead system by effectively simulating or functioning as an epicardial patch electrode. The branched electrode distribution can also be achieved with relatively little trauma during deployment (i.e., the electrodes can be relatively easily delivered to different and desired vasculature branches) since the lead system can be configured to control the magnitude and degree of the branch pattern during deployment.

Defibrillation through use of an electrode implanted in the middle cardiac vein and/or its tributaries also offers important advantages. Blood pressures in the middle cardiac vein are relatively low, so the presence of the lead system is tolerated by this cardiac vasculature. A defibrillation shock between electrodes implanted in the middle cardiac vein and the pulmonary artery [?] will effectively be straight up the middle of the heart. When used in connection with a lead system such as 10 having a plurality of electrodes spatially distributed throughout the branches of the middle cardiac vein, the efficacy of the defibrillation shock can approach that provided by an epicardial patch electrode straddling the inferior septum and its intersection with the left and right ventricular walls. Variations in shock configurations can also be achieved. All of these features can enable successful defibrillation with reduced defibrillation threshold energy (DFT) and enhance the efficacy of the overall defibrillation procedure.

Although the present invention has been described with reference to preferred embodiments, those skilled in the art will recognize that changes can be made in form and detail without departing from the spirit and scope of the invention.

What is claimed is:

1. A method for performing cardiac defibrillation in a human patient, comprising:
   implanting a plurality of electrodes in the patient, including implanting an electrode in a middle cardiac vein of the patient's heart by accessing the middle cardiac vein through the middle cardiac ostium without passing through the coronary sinus;
   implanting a cardioverter defibrillator for treating cardiac dysrhythmias in the patient and electrically interconnecting the defibrillator to the electrodes; and
   causing the cardioverter defibrillator to deliver electrical defibrillation countershocks to the patient's heart through the implanted electrodes, including the electrode in the middle cardiac vein.

2. The method of claim 1 wherein implanting a plurality of electrodes includes:
   providing a lead system including:
      a catheter shaft having a plurality of electrode channels;
      an electrode within each electrode channel; and
      a lead wire electrically interconnected to each electrode and extending through the catheter shaft, wherein the electrodes are movable between a retracted position within the electrode channel and a deployed position outside the channel;
   transvenously delivering and implanting the lead system in the patient's middle cardiac vein; and
   advancing the electrodes from the retracted position to a deployed position within the patient's middle cardiac vein.

3. The method of claim 2 wherein advancing the electrodes to the deployed position includes advancing at least one of the electrodes to a deployed position in a tributary to the middle cardiac vein.

4. The method of claim 3 wherein advancing the electrodes to the deployed position includes advancing a plurality of the electrodes to deployed positions in a plurality of tributaries to the middle cardiac vein.

5. A method of operating an implantable cardioverter defibrillator (ICD) for treating cardiac dysrhythmias in human patient, the ICD including a sealed housing structure constructed a bio compatible material containing a battery source of electrical energy, a high-voltage capacitor system and a control system which cooperate to deliver electrical countershocks to plurality of implanted electrodes, the method comprising:

implanting a plurality of electrodes in the patient, including an electrode in a middle cardiac vein of the patient's heart by accessing the middle cardiac vein through the middle cardiac ostium without passing through the coronary sinus;

electrically interconnecting the implanted electrodes to the ICD;

sensing cardiac signals representative of a heart rate;

operating the control system to evaluate the cardiac signals and detect cardiac dysrhythmias; and causing the ICD to deliver electrical countershocks through the implanted electrodes, including the electrode in the middle cardiac vein, in response to the detection of a cardiac dysrhythmia.

6. The method of claim 5 wherein implanting a plurality of electrodes includes:

providing a lead system including:
 a catheter shaft having a plurality of electrode channels;
 an electrode within each electrode channel; and
 a lead wire electrically interconnected to each electrode and extending through the catheter shaft, wherein the electrodes are movable between a retracted position within the electrode channel and a deployed position outside the channel;

transvenously delivering and implanting the lead system in the patient's middle cardiac vein; and advancing the electrodes from the retracted position to a deployed position within the patient's middle cardiac vein.

7. The method of claim 6 wherein advancing the electrodes to the deployed position includes advancing at least one of the electrodes to a deployed position in a tributary to the middle cardiac vein.

8. The method of claim 7 wherein advancing the electrodes to the deployed position includes advancing a plurality of the electrodes to deployed positions in a plurality of tributaries to the middle cardiac vein.

* * * * *